(12) United States Patent
Castillo

(10) Patent No.: US 6,894,078 B2
(45) Date of Patent: May 17, 2005

(54) ALCOHOL BASED TOPICAL ANESTHETIC FORMULATION AND METHOD

(76) Inventor: James G. Castillo, 15412 - 15th St., Lutz, FL (US) 33549

( * ) Notice: Subject to any disclaimer, the term of this patent is extended or adjusted under 35 U.S.C. 154(b) by 0 days.

(21) Appl. No.: 09/954,494

(22) Filed: Sep. 17, 2001

(65) Prior Publication Data

US 2003/0054017 A1 Mar. 20, 2003

(51) Int. Cl.[7] .......................... A61K 31/16; A61K 31/12
(52) U.S. Cl. ...................... 514/626; 514/676; 514/817; 514/818
(58) Field of Search ................................ 514/817, 818, 514/626, 676; 424/401, 45, 443

(56) References Cited

U.S. PATENT DOCUMENTS

| | | | | |
|---|---|---|---|---|
| 3,808,319 A | * | 4/1974 | Kanfoush | 514/544 |
| 4,091,090 A | * | 5/1978 | Sipos | |
| 4,557,934 A | * | 12/1985 | Cooper et al. | |
| 4,954,487 A | * | 9/1990 | Cooper et al. | |
| 5,415,866 A | * | 5/1995 | Zook | 424/448 |
| 5,667,799 A | * | 9/1997 | Caldwell et al. | 424/449 |
| 5,753,270 A | * | 5/1998 | Beauchamp et al. | 424/667 |
| 5,916,548 A | * | 6/1999 | Hutchins et al. | 424/70.12 |
| 5,993,836 A | * | 11/1999 | Castillo | |
| 6,046,187 A | * | 4/2000 | Berde et al. | |
| 6,299,902 B1 | * | 10/2001 | Jun et al. | 424/449 |
| 6,429,228 B1 | * | 8/2002 | Inagi et al. | 514/558 |
| 6,432,415 B1 | * | 8/2002 | Osborne et al. | 424/400 |
| 6,485,714 B1 | * | 11/2002 | Mangione et al. | 424/62 |

* cited by examiner

*Primary Examiner*—Vickie Kim
(74) *Attorney, Agent, or Firm*—Pendorf & Cutliff

(57) ABSTRACT

A method for applying a topical anesthetic to an area of skin comprising the steps of a) incorporating an anesthetic in a lipophilic base into a volatile solvent, to form a homogeneous solution; b) applying the homogeneous solution into the area of skin to be treated; and c) evaporating the volatile solvent from the homogeneous solution; wherein the volatile solvent is present in the formulation in amounts between 40–80%; and wherein said topical anesthetic rapidly penetrates the skin surface at said skin, leaving a cooling sensation on the skin. The topical anesthetic formulation contains a penetrating enhancer carrier that markedly enhances the delivery of the anesthetic across human skin without altering the acceptable delivery rate of the anesthetic that needs to be delivered through the skin and leaves a cooling sensation on the skin.

7 Claims, No Drawings

ALCOHOL BASED TOPICAL ANESTHETIC FORMULATION AND METHOD

BACKGROUND OF THE INVENTION

1. Field of the Invention

This invention relates to a topical anesthetic formulation comprising lidocaine and a volatile carrier/penetration enhancer. The formulation markedly enhances the delivery rate of the anesthetic, can be administered in a simple manner, and is free of side effects associated with many penetration enhancers. More particularly, the invention concerns a method of anesthetizing by using such a formulation.

2. Description of the Related Art

Historically, dermal anesthesia for minor skin surgery has been achieved by the injection of anesthetic solution via a needle and syringe. Although this technique is effective, it suffers from several drawbacks. Many patients, especially children, do not tolerate the pain of an injection well. Also, injection of topical anesthetic into an allergic patient could result in a severe reaction.

The state of the art shows an increase in the use of topical anesthetic over injected anesthetics. Topical anesthetics act via a loss of sensation in the localized area of administration in the body. The mechanism by which topical anesthetics induce their effect, while not having been determined definitively, is generally thought to be based upon the ability to topically interfere with the initiation and transmission of a nerve impulse, e.g., interfering with the initiation and/or propagation of a depolarization wave in a localized area of nerve tissue.

In recent years, creams containing a Eutectic Mixture of Local Anesthetics (EMLA®) such as lidocaine and prilocaine have been found useful as a topical anesthetic for superficial skin procedures. The EMLA® cream is applied to a lesion and adjacent tissue and covered with an occlusive dressing for about 20 minutes to about 2 hours. More recently, a formulation of 30% lidocaine in an acid mantle cream has been found to be an effective and inexpensive topical anesthetic.

While the EMLA® and topical lidocaine creams are welcome alternatives to anesthetic injection, they have several drawbacks. A major inconvenience is that local anesthesia of intact skin for minor procedures is not achieved until at least 60 minutes following application. For more invasive procedures, such as split skin graft harvesting, at least two hours may be required. This delay in onset is a significant disadvantage, as it is a great inconvenience for both patients and medical staff. Such delay is particularly a problem in the area of pediatrics, where any additional time spent awaiting treatment only contributes to the anxiety of the patient.

Another disadvantage with EMLA® cream is that, for deep penetrative effect, it is necessary that the cream be applied under an occlusive dressing. Specifically, a bilayer of laminate and absorbent cellulose is taped to the area of the skin to be anesthetized. Such a dressing is inconvenient and messy.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels to be so absorbed; molecules must overcome a different resistance to penetration in each type of tissue. Transport across the skin membrane is thus a complex phenomenon. However, it is the cells of the stratum corneum, which present the primary barrier to absorption of topical compositions or transdermally administered drugs.

This impermeability may be attributed to the nature of one very thin layer created by normal development and physiological changes in the skin. After cells are formed in the basal layer, they begin to migrate toward the skin surface, until they are eventually sloughed off. As they undergo this migration, they become progressively more dehydrated and keratinized. When they reach the surface, just prior to being discarded, they form a thin layer of dense, metabolically inactive cells approximately ten microns (10–15 cells) thick, the stratum corneum or "cornified layer." As a result of the high degree of keratinization of the cells, which comprise the stratum corneum, a formidable barrier is created. Absorption through a mucosal surface is generally efficient because the stratum corneum is absent. Therefore, any formulation to be utilized as an efficient topical, transdermal anesthetic must be capable of being readily absorbed through the skin.

In addition to the thickness and integrity of the stratum corneum epidermis, percutaneous or transdermal absorption can significantly alter drug kinetics and depend on a variety of factors including site of application, size of active drug molecule, permeability of the membrane of the transdermal drug delivery system, state of skin hydration, pH of the drug, drug metabolism by skin flora, lipid solubility, and alteration of blood flow in the skin by additives and body temperature.

To increase the rate of penetration of drugs across the skin, the prior art shows the use of various skin penetration enhancers. Currently available percutaneous and transmucosal penetration enhancers use solvents or detergents to alter the physical properties of the multilayered lipid bilayers. Such agents include dimethylsulfoxide (DMSO), oleyl alcohol (OA), propylene glycol (PG), methyl pyrrolidone and AZONE® (dodecylazyl cycloheptan 2-one). However, unfortunately, the uses of the known penetration enhancers are associated with disadvantages.

For one, the penetration enhancer is typically co-administered with the desired drug. That is, the penetration enhancer passes through the patient's skin at the same time the drug does. Depending upon the exact nature of the penetration enhancer, this can lead to side effects related directly to the penetration enhancers.

Another disadvantage is that the addition of penetration enhancers tends to change the concentration of the drug, which presents the problem of difficulties in achieving an acceptable delivery rate of the medicament that needs to be delivered through the skin.

Another disadvantage is that the enhancers are often organic solvents, which can, in some cases, react with and alter the character of the drug being delivered. In addition, the enhancers can interact with the patient's skin, in some cases causing irritation and the like.

U.S. Pat. No. 5,415,866 entitled "Topical Drug Delivery System" to Zook discloses a topical anesthetic including a eutectic mixture of lidocaine and prilocaine and a high amount of alcohol. The Zook reference teaches the use of an occlusive dressing to prevent the desiccation of the drug. A disadvantage of the Zook invention is that the alcohol is co-administered with the drug and passes through the patient's skin at the same time the drug does, which can lead to side effects or, in the case of adulterated alcohol, discomfort. Another disadvantage is that the alcohol can interact with the patient's skin for extended periods and cause irritation and the like. Another disadvantage associated with the use of an occlusive dressing is that the drug is applied "under cover" and gives no direct stimulus to the patient. It is difficult for the patient to know when or if the anesthetic is taking effect. Further, without some form of psychological stimulus, the patient may not become mentally receptive to becoming anesthetized.

Further representing the state of the art is U.S. Pat. No. 5,993,836, owned by the same inventor, which is incorporated herein by reference. The patent discloses a topical anesthetic formulation including, e.g., lidocane (15%), prilocane (5%), and dibucaine (0.75%) as anesthetics; phenylephrine as vasoconstrictor; and a lipophilic base. Lidocane and prilocane form a eutectic mixture, and the formulation is incorporated in a lipophilic base. While representing an improvement over prior art topical anesthetic formulations, there remains a need for further improvement in delivery rate of the anesthetic, ease of administration, and patient acceptance.

SUMMARY OF THE INVENTION

It has now been surprisingly discovered that the above problems can be overcome, and that a topical, transdermal anesthetic comprising lidocaine can be surprisingly enhanced, by the addition of a volatile carrier/penetration enhancer, preferably a low carbon alcohol, to the anesthetic formulation.

Upon application to the skin of a patient, and prior to evaporating, the alcohol acts as a penetration enhancer that increases the permeability of the skin, preparing the skin so that the rate at which the anesthetic drug diffuses through the skin and enters the tissues and bloodstream will be increased. The alcohol alters the physiochemical nature of the stratum corneum to reduce its diffusional resistance.

Then, after the skin resistance has been altered, after the skin is initially rendered cool and anesthetized, and after much of the alcohol has evaporated, the kinetics of the formulation change so that, as the proportion of remaining alcohol is reduced, a more concentrated anesthetic formulation remains present on the skin, which brings about a more advanced level of anesthetization.

As a side benefit, the evaporation of the alcohol cools the skin. This causes the patient to feel a soothing, cool, numbing feeling, which psychologically prepares the patient to the effects of the anesthetic. In many patients, this tactile input synergistically enhances pain tolerance.

Further, the low carbon alcohol used as volatile carrier in the present invention is non-toxic, is evaporated after a short time, and thus has a much lower likelihood of inducing skin irritation.

Thus, by using the formulation of the present invention, the delivery rate of the anesthetic is markedly enhanced, the method of administration remains simple, the incidence of side effects associated with many penetration enhancers is reduced or eliminated, topical irritation is avoided, and the comfort level of the patient is increased as the patient has the perception that the formulation is taking effect.

The invention further provides a method of anesthetizing, comprising the topical administration of a formulation comprising lidocaine in a lipophilic base dissolved in a volatile solvent in which the mixture is soluble and which is generally recognized as safe for topical application to the skin.

A further advantage according to the method of the present invention is that it does not require the step of de-fatting the skin with alcohol prior to the application of the anesthetic, thus skin irritation is avoided.

The present invention also comprises a process comprising the steps of mixing lidocaine in a lipophilic base with a volatile penetration enhancer carrier and applying the mixture to the skin.

Low carbon alcohols have a relatively low value of heat of vaporization, which makes them able to evaporate quickly at room temperature. It is this characteristic that gives the user the "cooling" sensation realized during application. In order to feel the cool sensation, it is necessary that the alcohol be present in the composition at high concentrations.

The present formulation and method are particularly useful in preparing for ablation, and prior to laser procedures requiring vaporation, excision, incision, and coagulation of soft tissue in medical specialties including dermatology, plastic surgery, podiatry, neurosurgery, gynecology, otorhinolaryngology (ENT), arthroscopy (knee surgery), and invasive and endoscopic general surgery.

In its basic embodiment, the present invention is directed to a method for applying a topical anesthetic to an area of skin, the method comprises the steps of:

a) incorporating lidocaine in a lipophilic base into a volatile solvent, to form a homogeneous solution;

b) applying the homogeneous solution into the area of skin to be treated; and c) evaporating the volatile solvent from the homogeneous solution;

wherein the volatile solvent is present in the formulation in an amount between 40–80%.

In the present invention, incorporating comprises dissolving the lidocaine in lipophilic base into a volatile solvent.

Evaporating is carried out until less than 5 wt %, preferably less than 1 wt %, of the volatile solvent remains in the solution.

In a first preferred embodiment, the present invention further comprises a thickener, such as carbopol 940, from 0.5% to 2% and an emulsifier, such as polysorbate 80, from 0.5% to 2% of the weight of the total formulation.

In a second preferred embodiment, the topical anesthetic, comprises (all percentages being by weight):

from about 40–70% alcohol;

from about 3–40%, preferably about 20% lidocaine;

from about 0.5 to 2%, preferably about 1.5% thickener;

from about 0.5 to 2%, preferably 1.5% emulsifer;

from about 20–40%, preferably 30% water; and the balance being a lipophilic base;

Accordingly, the lipophilic based formulation of the present invention is one which contains no, or substantially no, aqueous component or aqueous functional-equivalent. Further, for the purposes of the present invention, the definition of lipophilic base is not particularly limited, and any of those known in the pharmaceutical and cosmetic industries may be employed, and includes lipophilic materials modified with thickeners, thinners, stabilizers, surfactants, etc.

The present method may be used for minor surgery procedures, such as cosmetic applications, which include, but are not limited to, laser resurfacing, electrolysis, permanent makeup application, body piercing, and tattooing.

In addition, the method of the present invention can be used on preemptive anesthesia and in post-operative pain relief therapy, especially in pediatrics and overly emotional patients.

The present invention relates to improved formulations and methods for the skin delivery of anesthetics to human and animal tissue and systems. The invention provides penetrating topical formulations and therapies, and is based on the use of a pharmaceutically-active agent dissolved in, or admixed with, a novel volatile penetration-enhancing carrier.

The formulations of this invention comprise a safe and effective amount of an anesthetic, together with a volatile penetration-enhancing carrier that when contacted with patient skin, allows the volatile carrier to evaporate leaving the skin with a cool sensation, anesthetized and with more concentrated anesthetic present on the skin.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other anesthetic formulations. It should also be realized by those skilled in the art that such equivalent formulations do not depart from the spirit and scope of the invention set forth in the appended claims.

DETAILED DESCRIPTION OF THE INVENTION

In this invention, the effective amount of anesthetic will mean that amount of anesthetic needed to produce a therapeutic dose following its transdermal administration.

An advantage, as well as a major distinguishing feature, of the method and formulation of the present invention is attributable to the presence of volatile penetration enhancers that when contacted with patient skin, evaporates leaving the skin cool (psychological effect), anesthetized and with more concentrated anesthetic present on the skin.

Penetration Enhancers

A penetration enhancer is an agent used to increase the permeability of the skin to a pharmacologically active agent to increase the rate at which the drug diffuses through the skin and enters the tissues and bloodstream. A chemical skin penetration enhancer increases skin permeability by reversibly damaging or by altering the physiochemical nature of the stratum corneum to reduce its diffusional resistance. In a review of the technical and patent literature, more than 275 different chemical compounds were found to be cited as skin penetration enhancers. Most of the compounds are generally recognized as safe (GRAS) ingredients that would often be considered inert by a formulator. Osborne D W, Henke J J, Pharmaceutical Technology, November 1997, pp 58–86. Examples of penetration enhancers include: alcohols, such as methanol, ethanol, although it is conceivable that denatured ethyl alcohol may be used alternatively, isopropyl alcohol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof.

The selection of the penetration enhancer is made by the practitioner depending on, for example, the solubilities of each component, which may be included in the formulation.

The present invention prefers the use of an alcohol, preferably a low carbon alcohol, because low carbon alcohols have a relatively low value of heat of vaporization with made them able to evaporate quickly at room temperature. It is this characteristic that gives the user the "cooling" sensation realized during application. In order to feel the cool sensation, the alcohol needs to be present in the composition at high concentrations.

A number of patents disclose the use of penetration enhancers to deliver medications transdermally. Grasela et al, U.S. Pat. No. 5,837,289 entitled "Transdermal Delivery of Medications using a Combination of Penetration Enhancers," discloses the use of at least two separate penetration enhancers in a cream to deliver an extensive list of medications. In U.S. Pat. No. 5,238,933 entitled "Skin Permeation Enhancer Compositions" to Catz et al, disclose a skin penetration enhancer formulation comprising a lower aliphatic ester of a lower aliphatic carboxyl acid in combination with a lower alkanol to administer an active agent. In U.S. Pat. No. 5,229,130 entitled "Vegetable Oil-Based Skin Permeation Enhancer Compositions, and Associated Methods and Systems" to Sharma et al. disclose a vegetable oil-based skin penetration enhancer to deliver active agents through the skin. U.S. Pat. No. 4,933,184 entitled "Menthol Enhancement of Transdermal Drug Delivery," discloses a transdermal formulation that uses methanol either sequentially or simultaneously to deliver drugs.

While there are a number of patents and publications available that relate to the transdermal administration of drugs and to skin permeation enhancer compositions, Applicant is unaware of any art that suggests that the combinations now disclosed herein provide a synergistic enhancing effect.

The present invention takes advantage of the use of a volatile penetration enhancer that when contacted with patient skin evaporates, leaving the skin cool (psychological effect), anesthetized and with more concentrated anesthetic present on the skin.

Topical Anesthetic

Two major classes of topical anesthetics used in the nonprescription treatment of pain are esters and amides. Examples of those in the ester class include benzocaine, butamben picrate and tetracaine. Examples of those in the amide class are dibucaine, prilocaine, etidocaine, mepivacaine, bupivicaine and lidocaine. Other examples are proprionic acid derivatives, fenamates, pyrrolealkanoic acids, pyrazolone derivatives, oxicams, pramoxine, and others and mixtures thereof.

The present invention used lidocaine in a lipophilic base and a volatile pentration enhancer. Lidocaine is an amide-type topical anesthetic agent that stabilizes neuronal membranes by inhibiting the ionic fluxes required for the initiation of and conduction of impulses, thereby effecting topical anesthetic action. Lidocaine has a short latency period, long duration of action, and low toxicity. Lidocaine is chemically designated as an acetamide, 2-(diethylamino)-N(2,6-dimethylphenyl) and has an octanol:water partition ratio of 43 at pH 7.4.

By topically applying lidocaine to the skin, the first-pass effect in the liver, where lidocaine is metabolized, is avoided and the bioavailability is increased.

Lipophilic Base

As lipophilic base, the present invention is not particularly limited, and any of those known in the pharmaceutical and cosmetic industries may be employed, and includes lipophilic materials modified with thickeners, thinners, stabilizers, surfactants, etc. As lipophilic materials, an oleaginous material such as petrolatum, mineral oil thickened or gelled with polyethylene, high molecular weight paraffin waxes, mono and diglycerides of fatty acids gelled with high molecular weight fatty acids or polyamide complex of hydroxystearate, propylene glycol isostearate or isostearyl alcohol gelled with high molecular weight fatty acids and mixtures thereof may be used.

The lipophilic base should satisfy the following characteristics:

the base must allow the oils, and particularly the anesthetic, to be completely miscible therein;
the base must be compatible with the skin with the least possible number of adverse reactions;
the base must be smooth and pliable with no adverse odor;
the base should have a color appealing to the consumer;
the base must be stable and must provide a stable vehicle for the medication;
the base should be hydrophobic, i.e., have a low water absorbing capacity; and
the base should be able to readily release the medication incorporated therein into the skin.

Preferably, the lipophilic component is a higher aliphatic alcohol, preferably of 8–18 carbon atoms, or an ester thereof. Examples of oleagenous (lipophilic) ointment bases include White Ointment USP, Yellow Ointment NF, Oleic Acid USP, Olive Oil USP, Paraffin USP, Petrolatum NF, White Petrolatum USP, Spermaceti Wax USP, Synthetic Spermaceti NF, Starch Glycerite NF, White Wax USP, and Yellow Wax USP.

Thickener

Optionally, but preferably, thickeners can be added to the composition of the present invention. Examples of suitable thickeners include, but are not limited to, naturally-occurring polymeric materials such as sodium alginate, xanthan gum, quince seed extract, tragacanth gum, starch and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polyacrylamide polymers, polymethacrylic acid polymers, polyvinyl acetate polymers, polyvinyl chloride polymers, polyvinylidene chloride polymers and the like. Inorganic thickeners may also be used such as aluminium silicates, for example, bentonites, or a mixture of polyethylene glycol and polyethylene glycol stearate or distearate. Crystalline hydroxy containing waxes such as trihydroxystearin are also useful.

Also useful herein are hydrophilic gelling agents such as the acrylic acid/ethyl acrylate copolymers and the carboxyvinyl polymers sold by the B. F. Goodrich Company under the trademark of Carbopol resins. These resins consist essentially of a colloidally water-soluble polyalkenyl polyether crosslinked polymer of acrylic acid crosslinked with from 0.75% to 2.00% of a crosslinking agent such as polyallyl sucrose or polyally pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule.

Preferred for use herein are carbomers such as Carbopol 980, Carbopol 940, Carbopol Ultrez 10, Carbopol ETD2020 and mixtures thereof.

The viscosity of the final gel is dependent on the polymer molecular weight, as well as the concentration of the polymer in the vehicle or formulation.

The thickener is preferably present at a concentration of from about 0.5% to about 2.0%, preferably from about 0.8% to about 1.8%, and more preferably 1.5%. Mixtures of the above thickeners may also be used.

Emulsifiers

The compositions herein can comprise various emulsifiers. These emulsifiers are useful for emulsifying the various carrier components of the compositions herein. Suitable emulsifiers can include any of a wide variety of nonionic, cationic, anionic, and zwitterionic emulsifiers disclosed in the prior patents and other references. See McCutcheon's, Detergents and Emulsifiers, North American Edition (1986), published by Allured Publishing Corporation incorporated herein by reference in their entirety.

The emulsifier chosen should preferably be non-ionic to minimize irritation, and one skilled in the art can conduct tests to routinely select specific surfactants for this purpose.

Suitable emulsifiers can include, but are not limited to, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

The emulsifiers can be used individually or as a mixture of two or more and can comprise from about 0.5% to about 2.0%, preferably from about 0.8% to about 1.8%, and more preferably 1.5%.

When applied to intact skin, the formulation of the present invention provides dermal anesthetic by the release of lidocaine from the formulation into the epidermal and dermal layers of the skin and the accumulation of lidocaine in the vicinity of dermal pain receptors and nerve endings.

In addition to the above-described preferred embodiment, which contains lidocaine alternative embodiments include all formulations comprising lidocaine in a lipophilic base, a thickener such as carbopol 940, and an emulsifier such as polysorbate 80 dissolve in alcohol.

The mixture of lidocaine in a lipophilic base and a volatile penetration enhancer are deposited on the skin by any of the usual methods known to the art of applying topical formulations. In particular, it is preferred to apply the mixture dissolved in a volatile solvent (e.g. alcohol). When the resulting formulation is applied to the skin, the volatile solvent will evaporate, at the same time that acts as a penetration enhancer, cooling the skin and psychological producing in the patient the same imminent relief produced by injecting the anesthetic.

The present invention will, in the following, be described more in detail with reference to a number of examples.

EXAMPLE 1

The formulation, according to the invention, was made in the following manner (total quantity: 600 g):

a) 6.276 g of CARBOPOL 940 were weighed out and dissolved in 120 ml of distilled water heated to 45° C.

b) Once the CARBOPOL 940 was dissolved, 6 ml of POLYSORBATE 80 were added to the CARBOPOL 940.

Petrolatum was heated at 45° C., and the 30 g of lidocaine were dissolved in the heated Petrolatum.

The product of step (c) was added to the product of step (b).

The product of step (d) was dissolved in 490 ml of Isopropyl alcohol by whipping constantly the mixture.

EXAMPLE 2

Method of application of the formulation to the skin:

A thin layer of the product of Example 1 was applied using a cotton tipped applicator;

The alcohol was evaporated from the skin.

The patient rested for 30 to 45 minutes while waiting for the anesthetic to take effect. The patient experienced desensitization and good anesthetization.

The duration of desensitization was found to vary with the amount of product applied and the length of the waiting period. The minimum time reported was 1 hour, and the longest reported was three hours. The average desensitization period reported was 1½ hours.

EXAMPLE 3

Example 1 was repeated, but instead of using Lidocaine alone, a Eutectic mixture containing 5% of each Lidocaine and Prilocaine was used.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

Therefore, the foregoing is considered as illustrative only of the principles of the invention. Further, since numerous modifications and changes will readily occur to those skilled in the art, it is not desired to limit the invention to the exact formulation and operation shown and described, and accordingly, all suitable modifications and equivalents may be resorted to, falling within the scope of the invention.

Now that the invention has been described,

What is claimed is:

1. A method for enhancing an anesthetic effect by applying a topical anesthetic to an area of skin, the method comprising the steps of:

a) forming a homogeneous solution by dissolving into a volatile solvent an anesthetic in a lipophilic base, the lipophilic base selected from the group consisting of White Ointment USP, Yellow Ointment NF, Oleic Acid USP, Olive Oil USP, Paraffin USP, Petrolatum NF, White Petrolatum USP, Spermaceti Wax USP, Synthetic Spermaceti NF, Starch Glycerite NF, White Wax USP, and Yellow Wax USP;

b) applying the homogeneous solution into the area of skin to be treated; and c) evaporating the volatile solvent from the homogeneous solution;

wherein the homogenous solution includes
      from about 40–80% of the volatile solvent;
      from about 3–40% of the anesthetic;
      from about 0.5 to about 2.0 of a thickener;
      from about 0.5 to about 2.0 of an emulsiifer; and
      the balance being the lipophilic base wherein the anesthetic is chosen from benzocaine, butambenpicrate, tetracaine, dibucaine, prilocaine, etidocaine, mepivacaine, bupivicaine, lidocaine, proprionic acid derivatives, fenamates, pyrrolealkanoic acids, pyrazolone derivatives, oxicams, pramoxine, an eutetic mixture of lidocaine and prilocaine, or mixture thereof.

2. The method of claim 1, wherein incorporating comprises dissolving the anesthetic in lipophilic base into a volatile solvent.

3. The method of claim 1, wherein the anesthetic is lidocaine.

4. The method according to claim 1, wherein said volatile solvent is an alcohol.

5. The method of claim 1, wherein evaporating is carried out until less than 1 wt % of the volatile solvent remains in the solution.

6. The method according to claim 1, wherein said volatile solvent is isopropyl alcohol.

7. The method according to claim 1, wherein said volatile solvent is selected from the group consisting of isopropyl alcohol and denatured ethyl alcohol.

\* \* \* \* \*